(12) United States Patent
Kumar et al.

(10) Patent No.: US 11,027,019 B2
(45) Date of Patent: Jun. 8, 2021

(54) METHODS OF MAKING ANTIMICROBIAL BIOPOLYMER FROM SODIUM ALGINATE AND ALGAE EXTRACT USING AMINOGLYCOSIDES, AND METHODS OF USING THE SAME

(71) Applicant: Colorado School of Mines, Golden, CO (US)

(72) Inventors: Lokender Kumar, Golden, CO (US); John Brice, Aurora, CO (US); Linda Toberer, Golden, CO (US); Judith Klein-Seetharaman, Golden, CO (US); Daniel Knauss, Golden, CO (US); Susanta Kumar Sarkar, Highlands Ranch, CO (US)

(*) Notice: Subject to any disclaimer, the term of this patent is extended or adjusted under 35 U.S.C. 154(b) by 0 days.

(21) Appl. No.: 16/670,558

(22) Filed: Oct. 31, 2019

(65) Prior Publication Data

US 2020/0129622 A1 Apr. 30, 2020

Related U.S. Application Data

(60) Provisional application No. 62/753,647, filed on Oct. 31, 2018, provisional application No. 62/926,197, filed on Oct. 25, 2019.

(51) Int. Cl.
| | |
|---|---|
| *A61K 47/36* | (2006.01) |
| *A61K 9/70* | (2006.01) |
| *A61K 9/00* | (2006.01) |
| *A61K 31/702* | (2006.01) |

(52) U.S. Cl.
CPC ............ *A61K 47/36* (2013.01); *A61K 9/0014* (2013.01); *A61K 9/7007* (2013.01); *A61K 31/702* (2013.01)

(58) Field of Classification Search
CPC .... A61K 47/36; A61K 9/7007; A61K 9/0014; A61K 31/702
See application file for complete search history.

(56) References Cited

PUBLICATIONS

Kumar et al, Antimicrobial Polymer Formation from Sodium Alginate and Algae Extract Using Aminoglycosides, PLoS ONE 14(3): e0214411 (Year: 2019).*
"Treating Wounds with Absorbent Alginate Dressings," Advanced Tissue, 2015, retrieved from https://advancedtissue.com/2015/09/treating-wounds-with-absorbent-alginate-dressings/, 3 pages.
Dockery et al., "Lower extremity soft tissue and cutaneous plastic surgery," Saunders, Ltd., Philadelphia, PA, 2012, 495 pages. Submitted in 10 Parts.
Farrar, "Advanced wound repair therapies," Woodhead Publishing Limited, Cambridge, UK, 2011, 649 pages. Submitted in 7 Parts.
Gupta et al., "Textile materials and structures for wound care products," Advanced Textiles for Wound Care, 2009, pp. 45-96.
Kondaveeti et al., "Microbicidal gentamicin-alginate hydrogels," Carbohydrate Polymers, vol. 188, Apr. 15, 2018, pp. 159-167.

(Continued)

*Primary Examiner* — Carlos A Azpuru
(74) *Attorney, Agent, or Firm* — Sheridan Ross P.C.

(57) ABSTRACT

Methods of forming antimicrobial biopolymers from sodium alginate and algae extract using aminoglycosides are presented. Also presented are improved biopolymers, methods of making the biopolymers, and methods of using the biopolymers, wherein the biopolymer includes a sodium alginate and an aminoglycoside.

11 Claims, 15 Drawing Sheets
(11 of 15 Drawing Sheet(s) Filed in Color)

(56) References Cited

PUBLICATIONS

Maida, "Management of malignant wounds and pressure ulcers," Supportive Oncology, 2011, pp. 342-353.
Onishi et al., "Chapter 8: Novel textiles in managing burns and other chronic wounds," in Advanced Textiles for Wound Care, 2nd Edition, 2019, pp. 211-260.
Rajendran et al., "Chapter 2: Hi-tech textiles for interactive wound therapies," Handbook of Medical Textiles, 2011, pp. 38-79.
Schoukens, "Chapter 5: Bioactive dressings to promote wound healing," Advanced Textiles for Wound Care, 1st Edition, 2009, pp. 114-152.

* cited by examiner

METHODS OF MAKING ANTIMICROBIAL BIOPOLYMER FROM SODIUM ALGINATE AND ALGAE EXTRACT USING AMINOGLYCOSIDES, AND METHODS OF USING THE SAME

CROSS REFERENCE TO RELATED APPLICATION

This application claims priority and the benefit under 35 U.S.C. § 119(e) to U.S. Provisional Patent Application Ser. Nos. 62/753,647 filed Oct. 31, 2018, and 62/926,197 filed on Oct. 25, 2019, each of which are incorporated herein in their entirety by reference.

TECHNICAL FIELD

The present invention relates to methods of forming antimicrobial biopolymers from sodium alginate and algae extract using aminoglycosides. The present invention also relates to the improved biopolymers, methods of making the biopolymers, and methods of using the biopolymers.

BACKGROUND

According to the World Health Organization, the emergence of multidrug resistance among bacterial pathogens is a global public-health challenge. Such pathogens are responsible for infections of burn, wound, blood stream, nervous system, urinary, and respiratory tracts.

SUMMARY

Improved materials are needed for applications including drug delivery, wound dressing, cosmetics, cell adherence, tissue engineering, and finger print capture. The present invention addresses these needs, among others.

Materials such as biopolymers have been used as materials for drug delivery and wound dressing, and antimicrobial biopolymers can provide infection control properties. Biopolymers, including antimicrobial biopolymers, of the present disclosure can provide a source of biodegradable, sustainable, safe, and inexpensive materials used in drug delivery and wound dressing to control bacterial infections and improve wound healing, respectively.

The biopolymers disclosed herein include sodium alginate-based materials. The biopolymers may include a sodium alginate and an aminoglycoside. In various embodiments, antimicrobial alginate polymer from sodium alginate and aqueous extract of Wakame using antibiotic aminoglycosides. Thin layer chromatography of commercially available sodium alginate and Wakame extract showed similar oligosaccharide profiles. The sodium alginate may include *undaria pinnatifida*. The aminoglycoside may include one or more of kanamycin disulfate and neomycin sulfate. Various aminoglycosides, including gentamicin, neomycin, kanamycin, tobramycin, and streptomycin, were screened for their ability to induce polymerization, as discussed herein.

Methods to form the polymers disclosed herein may include providing an aqueous solution of sodium alginate and providing an aqueous solution of an aminoglycoside to produce the polymers. The methods may include where the aqueous solution of sodium alginate and the aqueous solution of the aminoglycoside are mixed. The sodium alginate may include *undaria pinnatifida*. The aminoglycoside may include one or more of kanamycin disulfate (KDS), neomycin sulfate (NS), gentamicin sulfate (GS), neomycin sulfate (NS), kanamycin sulfate (KS), kanamycin disulfate (KDS), tobramycin sulfate (TS), and streptomycin sulfate (SS). Methods of the present disclosure include a one-step synthesis of a sodium alginate biopolymer from aqueous Wakame algae extract and sodium alginate solutions using aminoglycoside antibiotics.

Advantages of the present invention include that Wakame is one of the most invasive species in the world and is obtained by well-established ocean farming technology, making the biopolymers of the present invention highly sustainable. The antimicrobial alginate biopolymers described herein are less expensive compared to other methods of making alginate biopolymers. The viscoelastic properties of the biopolymers allow for improved form fitting, and such improvements may be greater when the biopolymers are made using kanamycin disulfate. The improved properties may allow for flexible applications in wound dressing, cosmetics, cell adherence, tissue engineering, and finger print capture. In various embodiments, the slow release of antibiotics and the resulting zone of inhibition against *E. coli* DH5α were observed by agar well diffusion assay.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1A:
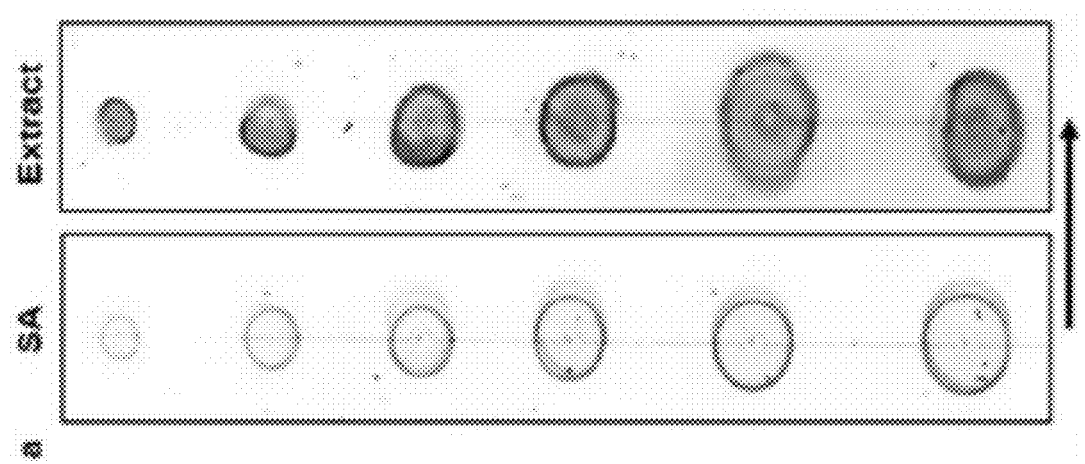
FIG. 1A shows illustrative thin layer chromatography (TLC) of commercial sodium alginate (SA) and Wakame extract oligosaccharide profiles.

The present invention relates to methods of forming antimicrobial biopolymers from sodium alginate and algae extract using aminoglycosides. The present invention also relates to the improved biopolymers, methods of making the biopolymers, and methods of using the biopolymers.

The terminology used herein is for the purpose of describing particular embodiments only and is not intended to be limiting, since the scope of this disclosure will be limited only by the claims.

As used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

Unless defined otherwise, all technical and scientific terms used herein have the same meaning as commonly understood by one of ordinary skill in the art to which this invention belongs. Although any methods and materials similar or equivalent to those described herein can also be used in the practice or testing of this disclosure, the preferred methods and materials are now described.

According to the World Health Organization (WHO), the emergence of multidrug resistance among bacterial pathogens is a global public-health challenge. Recently, the WHO has listed *Acinetobacter baumannii*, carbapenem-resistant *Pseudomonas aeruginosa*, and carbapenem-resistant Enterobacteriaceae as critical priority pathogens. These pathogens are responsible for various infections, including infections of burn, wound, blood stream, nervous system, urinary and respiratory tracts. Thus, antimicrobial biopolymer synthesis is one of the current areas of antimicrobial drug delivery research to control bacterial infection in biomedical devices, wound healing, food packaging, textiles, cosmetic products, and water treatment systems, among others. Furthermore, antimicrobial biopolymers are advantageously safer, less toxic and more efficacious than other compounds, including when compared to low molecular weight quaternary ammonium compounds. While some polymers have intrinsic antimicrobial activity, others have antimicrobial compounds attached to the polymer backbone or trapped within the polymer. Antibiotics can be trapped during polymerization reaction or by loosely bound cleavable linkages.

Long chain polysaccharides such as alginate are advantageous because they may be particularly suitable for polymer synthesis due to their biocompatibility, biodegradability, low cost, and non-toxicity to human cells. These properties cover an advantageously wide variety of uses in the biomedical and food industries. While chitosan and polylysine are biopolymers with intrinsic antimicrobial properties, alginate and other polysaccharides such as cellulose are not intrinsically antimicrobial in nature and require chemical incorporation of an antibiotic moiety.

Alginate, in particular, has gained interest because it is a sustainable polymer present in the cell walls of brown algae (Phaeophyceae), including *Undaria pinnatifida, Laminaria digitata, Laminaria hyperborea, Laminaria japonica, Macrocystis pyrifera*, and *Ascophyllum nodosum*. Alginate constitutes more than 50% of dry weight as lignin-free carbohydrate in Wakame (*Undaria pinnatifida*), a popular edible brown algae native to the Pacific Ocean and one of the hundred most invasive species in the world. In general, alginate may be used in applications including drug delivery, wound healing, and tissue engineering applications due to its advantageous biocompatibility, biodegradability, and ease of gelation.

Aminoglycosides have been an important class of antibacterial drugs especially for the treatment of Gram negative bacterial infections. These drugs show efficient post antimicrobial effects against pathogenic bacteria and maintain prolonged activity. Aminoglycosides target the protein translation machinery and bind reversibly to the bacterial 30s ribosomal subunit causing misreading of the genetic code and accumulation of non-functional truncated proteins leading to the death of bacteria. Aminoglycosides also show potential ototoxicity and nephrotoxicity, therefore, slow drug release using advanced drug delivery methods is clinically important. Embedding aminoglycosides in biopolymers such as hydroxypropyl methylcellulose (HPMC)/xyloglucan (XG) loaded with gentamicin sulfate has shown improved/high potency and thermal stability. Similarly, the integration of gentamicin sulfate with crosslinked collagen and sodium alginate crosslinked with $Ca^{2+}$ ions allowed controlled delivery of the antibiotic in treatment of postoperative bone infections. Tobramycin-alginate/chitosan polymeric nanoparticles (NPs) were shown effective in treatment of *P. aeruginosa* infections. Neomycin sulfate-loaded polyvinyl alcohol (PVA), polyvinyl pyrrolidone (PVP), and sodium alginate (SA) dressings have enhanced wound healing. In general, antimicrobial biopolymers made from polysaccharides are considered superior over synthetic polyesters or polyacrylic acid since these synthetic polymers have a risk of toxicity and a high cost of synthesis, for example. In this context, the carbodiimide chemistry is a viable strategy to chemically attach aminoglycosides to polysaccharides and has been used to attach gentamicin to alginate and chitosan. However, problematically, the carbodiimide chemistry involves several steps making it relatively expensive, in addition to the irreversible attachment of the aminoglycosides preventing release.

EXAMPLES 1-9

Example 1: Alginate Extraction from *Undaria pinnatifida* (Wakame)

Alginate was extracted from *Undaria pinnatifida* (Wakame) using mechanical grinding and orbital shaking. In particular, commercially available dry Wakame algae leaves were converted into powder using a coffee grinder. 20 grams (g) of dry powder was added to 500 milliliter (ml) water in an Erlenmeyer flask and incubated at 37° C. for 15 hours with 250 rotations per minute (rpm) orbital shaking. After incubation, aqueous sodium alginate supernatant was collected after centrifugation at 10000 rpm for 10 minutes (min). All steps were performed under sterile conditions to avoid microbial contamination. The supernatant was used for making alginate polymers using aminoglycoside antibiotics as described herein.

Example 2: Thin Layer Chromatography (TLC)

Sodium alginate and algae extract were spotted on TLC plates (Millipore, Cat #Hx71642853, TLC silica gel, 60 aluminum sheets, 20×20 centimeters (cm)) at several places using 5, 10, 15, 20, 25, and 30 microliter (μl) of solutions. TLC plates were developed using a mixture of 1-butanol, formic acid, and water in 4:6:1 volume to volume to volume (v:v:v) ratio. The developed TLC plates were heated at 110° C. for 5 min after spraying with 10% volumetric ratio (v/v) sulfuric acid in ethanol to test for the presence of alginate oligosaccharides.

Example 3: Screening of Aminoglycosides for Polymerization Reaction

Figure 1B:
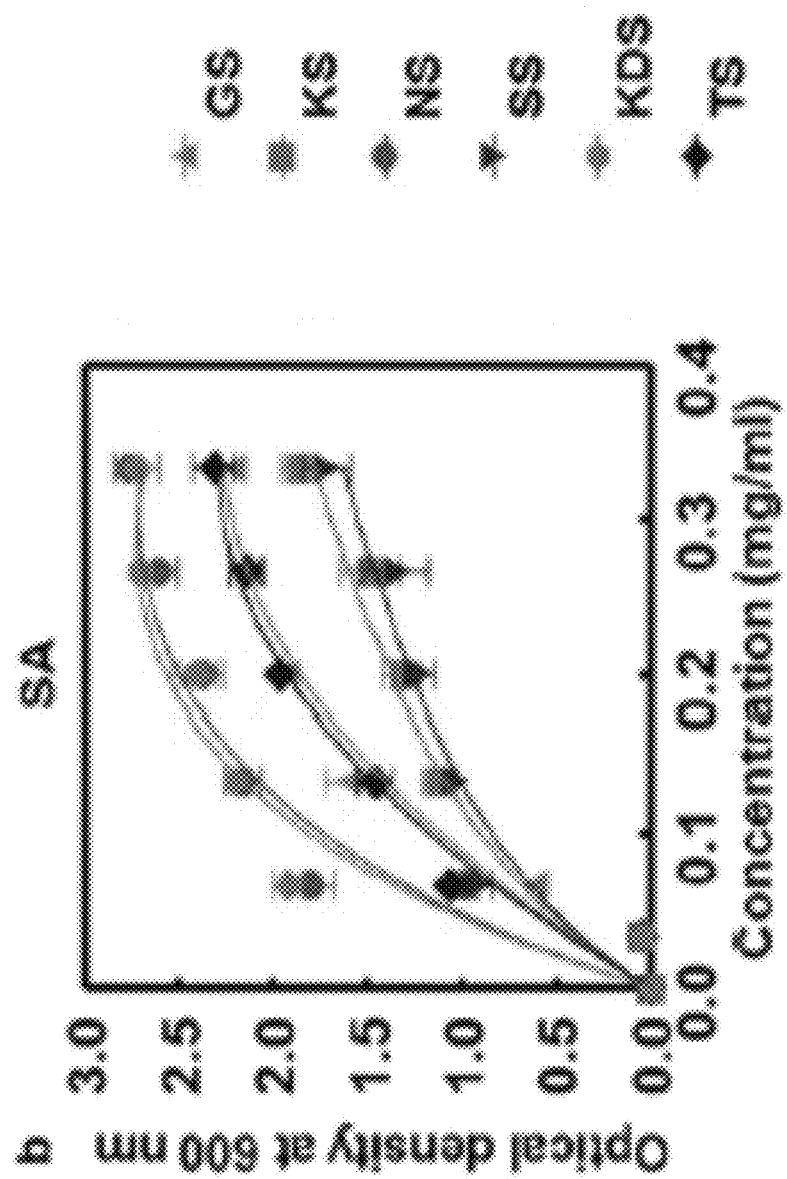
FIG. 1B shows illustrative optical density of commercial SA solution for different aminoglycosides.

Aminoglycosides were screened for polymerization reaction using optical density measurements. Six aminoglycosides were screened, namely, gentamicin sulfate (Sigma, Cat #G1914), neomycin sulfate (Sigma, Cat #PHR1491), streptomycin sulfate (Sigma, Cat #S6501), tobramycin sulfate (Sigma, Cat #T1783), kanamycin sulfate (Sigma, Cat #60615), and kanamycin disulfate (Sigma, Cat #K1876). 100 μl of 10 milligram per milliliter (mg/ml) aqueous solutions of antibiotics, 100 μl of deionized (DI) water, and either 100 μl of algae extract or 100 μl of 10 mg/ml sodium alginate (Sigma, Cat #W201502) were mixed together to obtain a total reaction volume of 300 μl in each well of 96-well microtiter plates. To vary the concentration of antibiotics, the subsequent wells were filled with 80 μl, 60 μl, 40 μl, 20 μl, and 10 μl of 10 mg/ml antibiotic stock solution with the remaining volume out of 300 μl reactions compensated by deionized (DI) water. Optical density at 600 nanometers (nm) (OD600) at room temperature was measured using a plate reader (BioTek, Model #Synergy2-Cam4, Software-Gen5-1.08). The results are shown in FIG. 1A, discussed further below. A Nikon Coolpix camera was used to image wells in microtiter plates, and the results are shown in FIG. 1B, discussed further below.

Example 4: Measurement of Melting Temperature of Alginate Polymer

Sodium alginate (20 mg/ml) was mixed with kanamycin disulfate (50 mg/ml) in a volume ratio of 1:1 ratio (10 ml each). Resultant solution with alginate polymer was centrifuged at 10,000 rpm for 10 min. The supernatant was discarded and the pellet was washed three times with 5 ml of sterile 0.1M (pH 7.4) phosphate-buffered saline (PBS) buffer. Six pellets were made and incubated with 2 ml of 1M NaOH at 10°, 20°, 40°, 60°, 80° and 100° C. for 30 min. After incubation, tubes were centrifuged at 10000 rpm for 10 min and absorption spectra of supernatants (as shown in FIG. 2) were measured using a spectrophotometer (Thermo Scientific Evolution 260 Bio Spectrophotometer).

Figure 3:
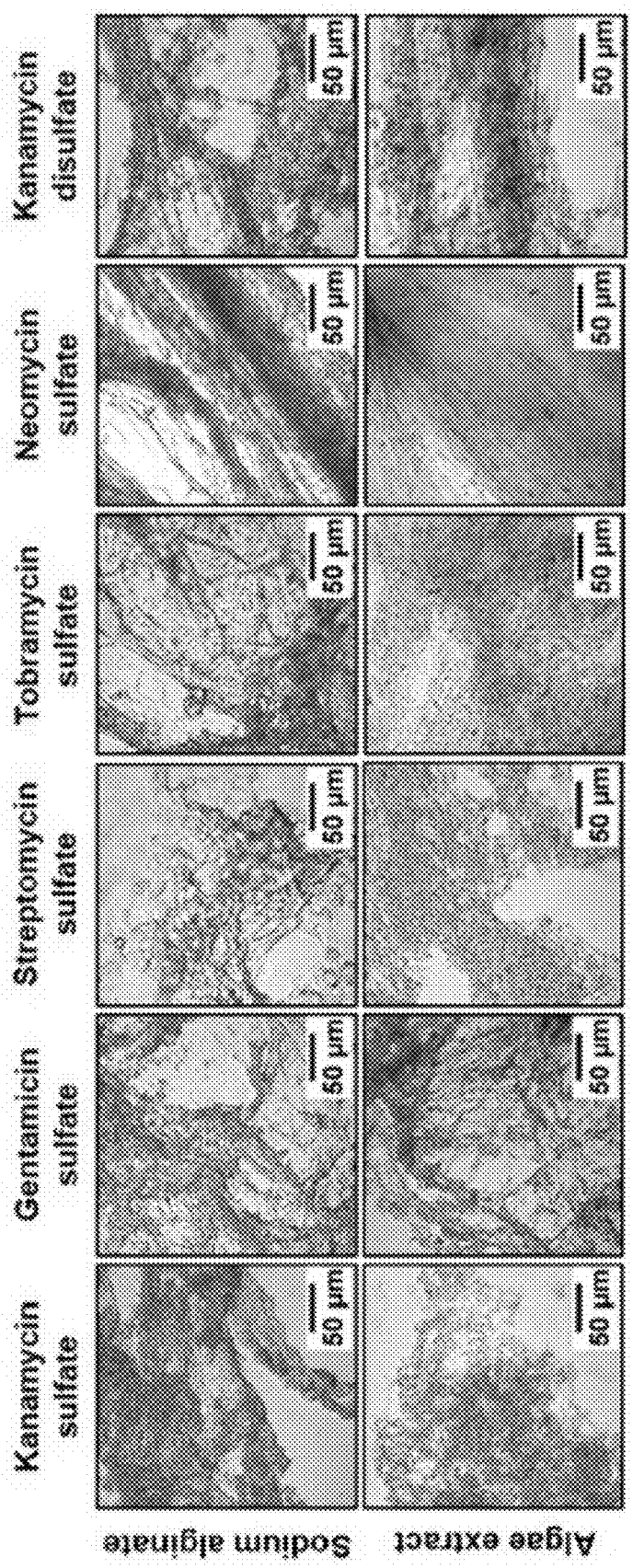
FIG. 3 shows illustrative textures of alginate polymers.

Example 5: Imaging and Analysis of Alginate Polymer Texture Using Light Microscope 100 μl of 10 mg/ml aqueous solutions of antibiotics were mixed drop-wise with either 100 μl of algae extract or 100 μl of 10 mg/ml sodium alginate on a clean glass slide. The immediate polymerization reaction was observed and imaged using a light microscope at 10 times (10×) magnification. The results are shown in FIG. 3.

The images were converted into 8-bit gray scale images with 256 gray levels to improve the quantitative description of the polymer texture. Using the gray scale values, i, four quantitative parameters of the Gray Level Co-Occurrence Matrix (GLCM) were determined using the ImageJ Texture Analyzer plugin: the energy, $E=\Sigma p(i,j)^2$; the contrast, $c=\Sigma |i-j|^2 p(i,j)$; the homogeniety, $H=\Sigma p(i,j)/(1+|i-j|)$; and the entropy, $S=-\Sigma p(i,j)\log[p(i,j)]$; where the sums are for all distinct gray scale values and $p(i, j)$ is the $(i, j)$th element of the normalized gray scale spatial dependence matrix.

Three images were chosen for each biopolymer, converted to 8-bit images, and analyzed with step size of one pixel at 0° angle. From the same 8-bit images, the fractal dimension was measured using the FracLac plugin for ImageJ by using the default settings of the FracLac program. All five parameters with standard deviations are given in Table 1 below.

Example 6: Scanning Electron Microscopy of Alginate Polymer

Biopolymer was made by mixing sodium alginate and kanamycin disulfate in a volume ratio of 1:1. The polymer suspension was spread on a clean glass slide and imaged using Phenom Pro-Scanning Electron Microscope (as shown in FIG. 4). In some embodiments, drying can lead to a loss of polymer flexibility and therefore, the images were captured quickly.

Example 7: Quantitative Weight-Based Assay of Polymer Formation

To quantify polymer formation, 500 μl of either 10 mg/ml aqueous sodium alginate solution or aqueous algae extract was added to a microcentrifuge tube and antibiotics were added at varying final concentrations. The reactions were vortexed and incubated for 10 min at room temperature. After incubation, tubes were centrifuged at 10000 rpm for 15 min and polymer pellets were weighed using an analytical balance. Weight of polymer pellets in milligram (mg) as a function of aminoglycoside concentrations in mg/ml were plotted as shown in FIG. 5, which were fitted to a model that also described the growth of pathogen prion protein growth. Fit parameters are given in Table 2 below.

Example 8: Antimicrobial Activity of Alginate Polymer

Antimicrobial activity of polymers was checked against *E. coli* DH5α using agar diffusion assay. Single colony of *E.* coli was inoculated in 10 ml of Luria Broth (LB) and incubated till OD600 reached 0.5 (log-phase culture) and 100 μl of bacterial culture was spread over LB agar plates. To check the antimicrobial activity of the antibiotics, wells were made by punching a hole in the LB agar plates. For reference plates, 50 μl of 10 mg/ml aqueous stock solution of each antibiotic was added in the wells as shown in the top row of FIG. 6.

For experiments with alginate polymers, polymer pellets were washed three times with sterile DI water to remove any unbound free antibiotics. Each washing step included the addition of 500 μl of sterile DI water and centrifugation at 10000 rpm for 15 min. After washing, polymer pellets were placed at the center of the LB plates with *E. coli* DH5α. Plates were incubated at 37° C. for 18 hours (hr). The zone of inhibition, e.g., the area with no growth of bacteria around well or polymer pellet, was measured using a ruler as shown in the middle and bottom rows of FIG. 6 and in Table 3 below.

Example 9: Biocompatibility Assay

Figure 7:
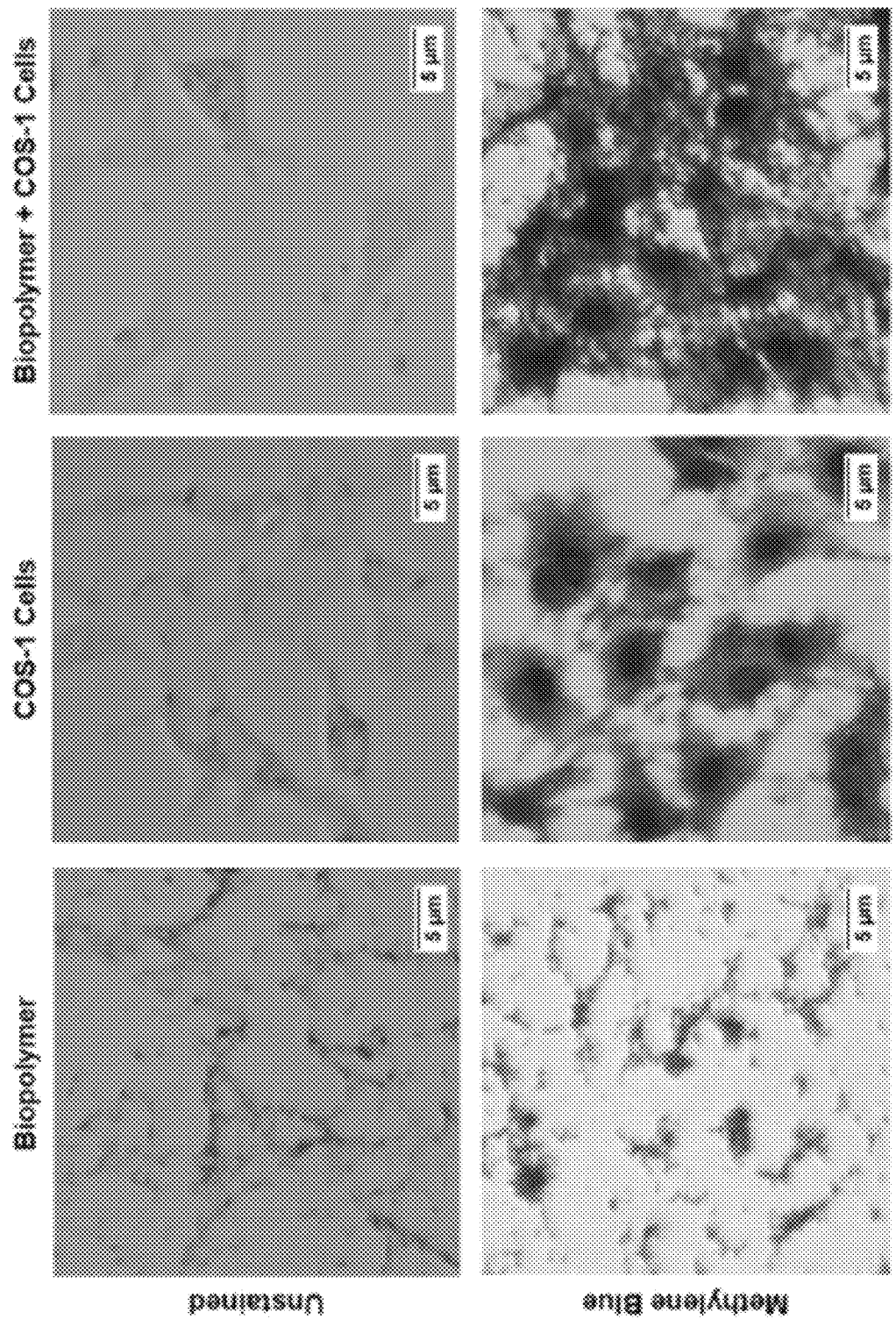
FIG. 7 shows illustrative biocompatibility of alginate polymer.

COS-1 cell lines were used to test biocompatibility of the antimicrobial alginate polymer. Sterile stock solutions of sodium alginate (10 mg/ml) and kanamycin disulfate (100 mg/ml) were mixed in a volume ratio of 1:1 in microtiter plate wells under sterile conditions. After 30 min incubation at 20° C., thin biopolymer layers were visible at the bottom of microtiter wells. The wells were washed three times with 2 ml of sterile 0.1M (pH 7.4) PBS buffer to remove unbound polymer. 1.5 ml of culture stock of COS-1 cells were added to the wells under sterile condition and incubated for 3 days at 37° C. at 5% $CO_2$ environment. After incubation, plates were imaged before and after staining with methylene blue using a light microscope and analyzed using ImageJ. The results are shown in FIG. 7.

The results of Examples 1-9 are described herein, and discussed further below are the results as they relate to oligosaccharides detection using TLC, quantification of polymerization efficiency, and quality of alginate polymers; polymer texture; amounts of polymer after centrifugation of polymerization reaction; and measurements of zone of bacterial inhibition to quantify the antimicrobial property of alginate-aminoglycoside polymer against *E. coli* DH5α.

Figure 1C:
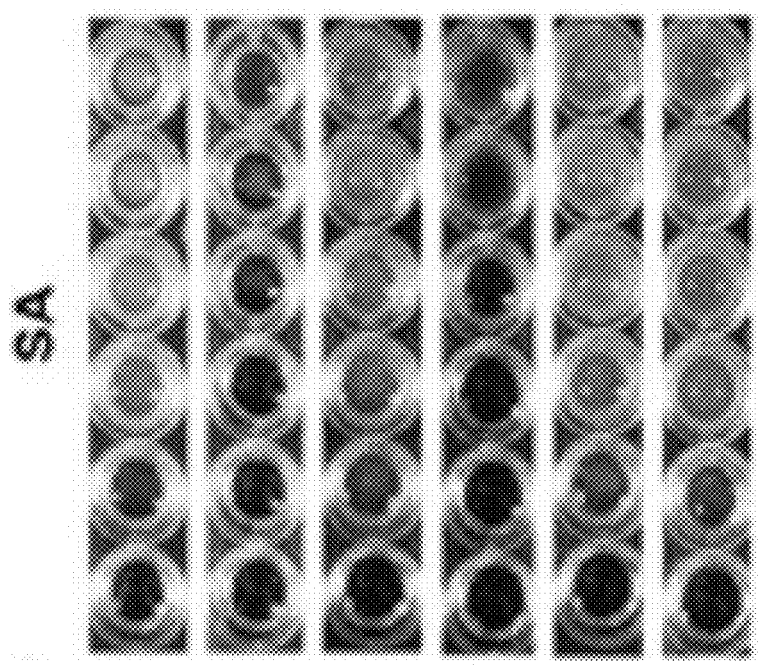
FIG. 1C shows an illustrative image of wells in a microtiter plate for commercial SA solution and different aminoglycosides.
Figure 1D:
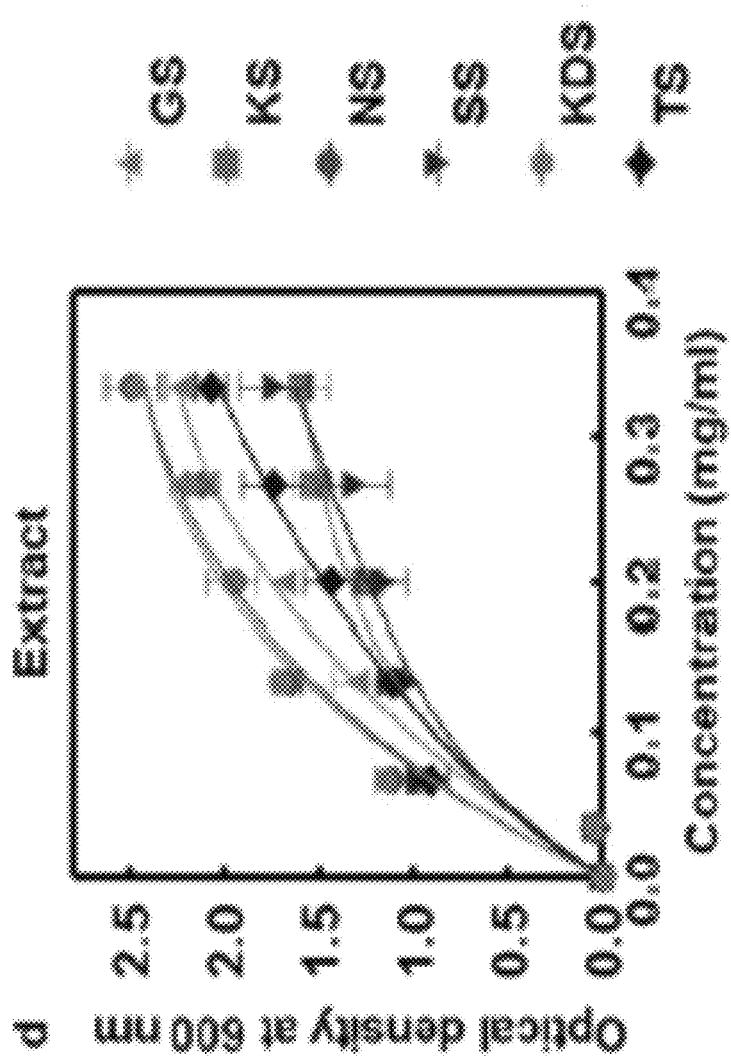
FIG. 1D shows illustrative optical density of Wakame extract solution for different aminoglycosides.

Illustrative oligosaccharides detection using TLC, quantification of polymerization efficiency, and quality of alginate polymers was analyzed. In particular, TLC was used to check the oligosaccharide profiles of commercial SA and aqueous Wakame extract and the results are shown in FIG. 1A. For quantifying polymerization efficiency, optical density (OD) at 600 nm was measured using a plate reader to quantify turbidity due to alginate polymerization to screen the six aminoglycosides as shown in FIGS. 1B-1D. Optical density, affected by both scattering and absorption, is a common technique to quantify cell growth, fluorophore concentration, and turbidity due to suspended particles. OD of the polymerization reactions at varying concentrations of aminoglycosides showed initial growth followed by saturation.

Figure 1E:
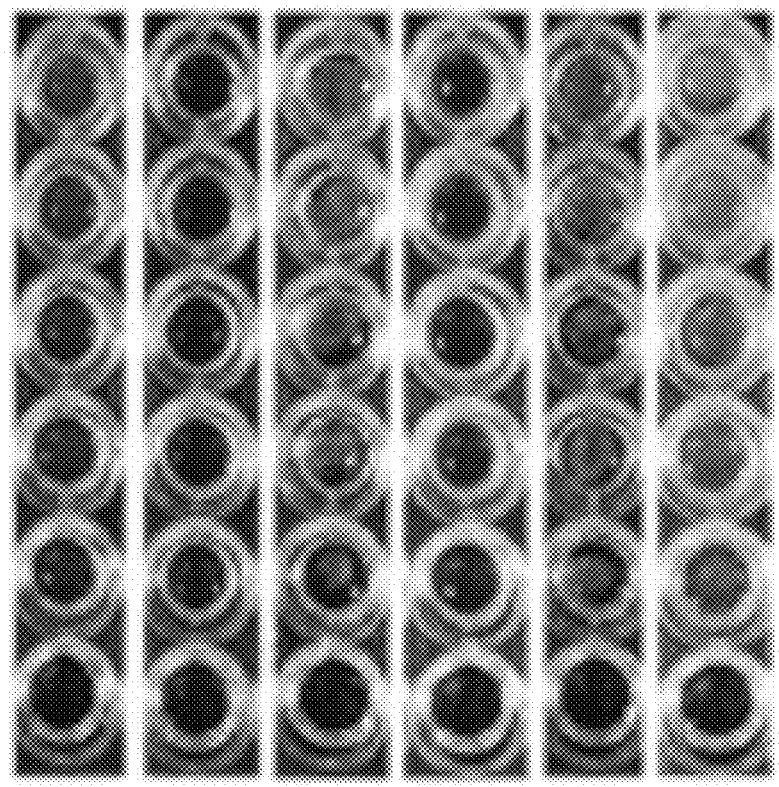
FIG. 1E shows an illustrative image of wells in a microtiter plate for Wakame extract solution and different aminoglycosides.
Figure 1F:
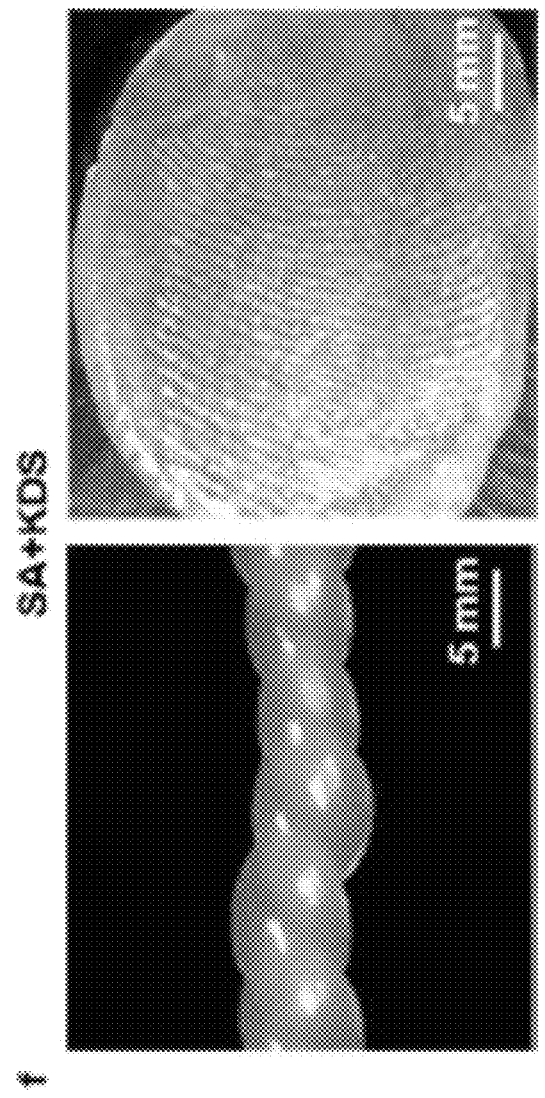
FIG. 1F shows illustrative malleability and form fitting alginate biopolymer using kanamycin disulfate (KDS)
Figure 1G:
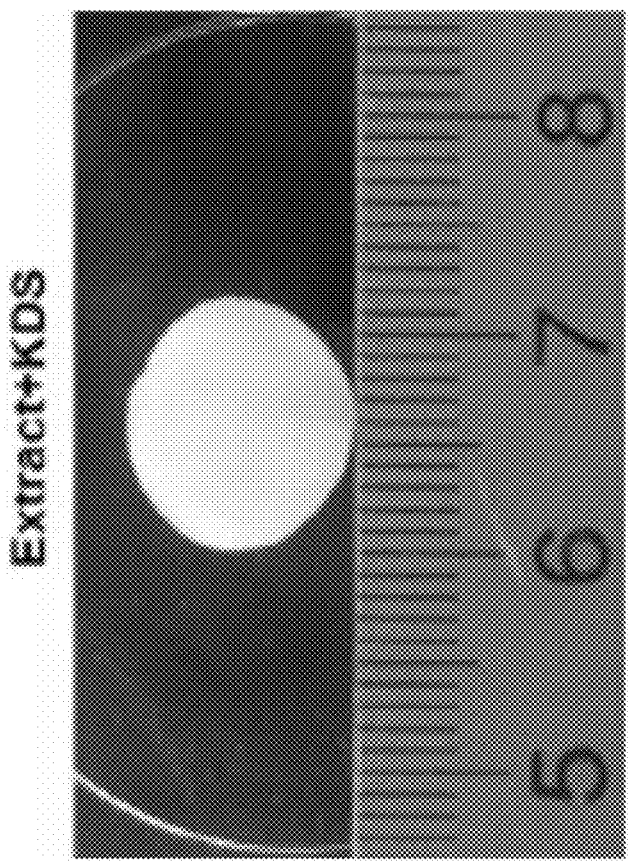
FIG. 1G shows an illustrative biopolymer made from Wakame extract using KDS.

FIGS. 1A-1G show, for example, illustrative quantification of efficiency of aminoglycosides in alginate polymerization for various embodiments. FIG. 1A shows TLC of commercial SA and Wakame extract with oligosaccharide profiles. In FIG. 1A, the black arrow shows the flow direction of the mobile phase. FIG. 1B shows the optical density of commercial SA solution for the different aminoglycosides; GS, KS, NS, SS, KDS, and TS. FIG. 1C shows an image of wells in a microtiter plate for a commercial SA solution and different aminoglycosides. For example, white turbidity led to higher optical density values as shown in FIG. 1C. FIG. 1D shows optical density of Wakame extract after addition of the different aminoglycosides. FIG. 1E shows an image of wells in a microtiter plate for Wakame extract solution and the different aminoglycosides. FIG. 1F shows malleability and form fitting alginate biopolymer using KDS. FIG. 1G shows biopolymer made from Wakame extract using KDS.

Further, FIG. 1F shows illustrative images of antimicrobial flexible and form fitting alginate biopolymer made using sodium alginate and kanamycin disulfate where the scale bar in FIG. 1F is 5 mm. Although other aminoglycosides can be used to make polymers from sodium alginate and algae extract, in various embodiments and as shown in FIG. 1F, kanamycin disulfate may advantageously make polymers that have improved flexibility and form fitting characteristics.

Using the data from FIGS. 1A-1G, the OD measurements were fitted to $y=ax/(k+x)$, which is a general equation describing ligand binding to substrate where k is the binding affinity. Fit parameters for aqueous solution of sodium alginate (as shown in FIG. 1B) were: $a=3.66\pm1.66$, $k=0.19\pm0.18$ (GS); $a=2.77\pm1.55$, $k=0.20\pm0.25$ (KS); $a=3.10\pm0.38$, $k=0.05\pm0.03$ (NS); $a=2.11\pm1.01$, $k=0.12\pm0.17$ (SS); $a=3.52\pm10.62$, $k=0.17\pm0.07$ (TS); $a=3.06\pm0.37$, $k=0.04\pm0.03$ (KDS). The fit parameters for aqueous Wakame extract (as shown in FIG. 1D) are: $a=4.00\pm1.35$, $k=0.26\pm0.16$ (GS); $a=2.04\pm0.67$, $k=0.10\pm0.08$ (KS); $a=3.59\pm0.78$, $k=0.16\pm0.09$ (NS); $a=2.62\pm2.34$, $k=0.22\pm0.42$ (SS); $a=3.28\pm1.61$, $k=0.23\pm0.89$ (TS); $a=3.48\pm0.60$, $k=0.15\pm0.07$ (KDS). The variable k was used as the measure of efficiency of aminoglycosides in polymerizing alginate. Neomycin and kanamycin disulfate resulted in the best polymerization. KDS was selected for further testing because it is relatively inexpensive and made alginate biopolymer from SA and Wakame extract, both of which resulted in good quality polymer (as shown in FIGS. 1F-1G); however, SA solution advantageously provided a more malleable (as shown in FIG. 1F, left panel) and form fitting (as shown in FIG. 1F, right panel) polymer.

Figure 2B:
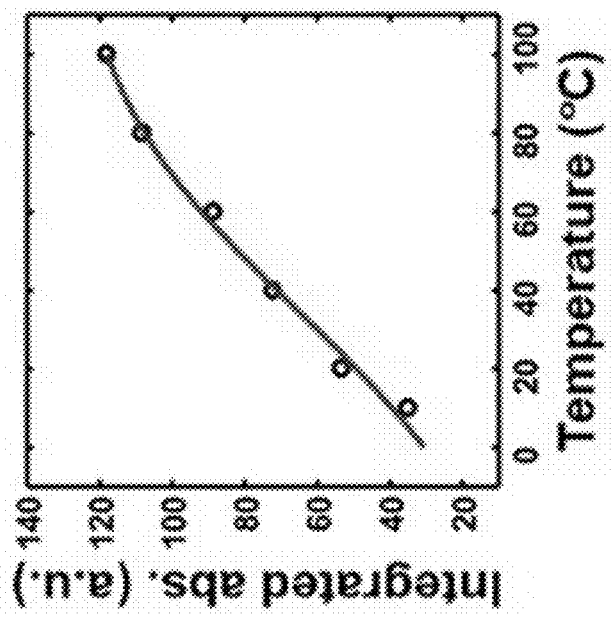
FIG. 2B shows an illustrative integrated absorption as a function of temperature for melting of antimicrobial alginate polymer.
Figure 2A:
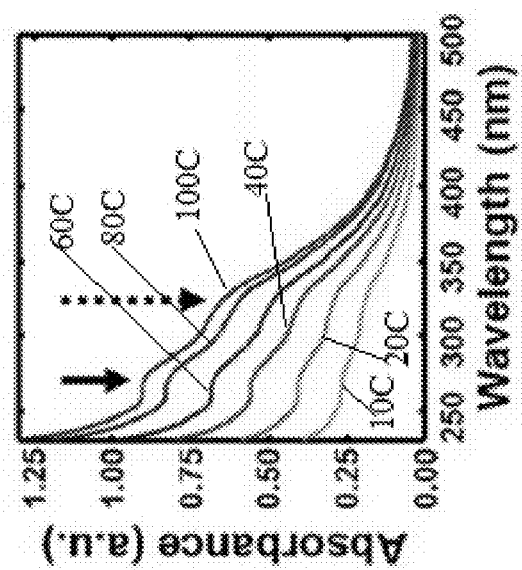
FIG. 2A shows an illustrative absorption spectra for melting of antimicrobial alginate polymer.

In FIG. 2A, absorption spectra of the centrifugation supernatant after incubation of the polymer in 1M NaOH solution for 30 min is shown at different temperatures. The peaks due to alginate and kanamycin disulfate are indicated by the solid and dotted black arrows, respectively. In FIG. 2B, the integrated absorption (open black circle) as a function of temperature shows that it fits well to a sigmoidal function (red line) with a melting temperature of 34.7±2.5° C. In FIGS. 2A and 2B, the melting temperature of the polymer was measured by leveraging temperature-dependent dissolution of alginate polymer. In particular, polymer was incubated in 1M NaOH solution to break ionic bonds in the polymer and dissolve the polymer. The reaction was centrifuged and absorption spectrum of the supernatant was measured. This was repeated at different temperatures (as shown in FIG. 2a). Integrated absorption (i.e., area under the absorption spectrum), as a function of temperature (as shown in FIG. 2b), was fitted to a sigmoidal function, $y=a/(1+\exp(T_m-T)/\sigma)$, where $T^m$ is the melting temperature and $\sigma$ is the width. The fit parameters are: a=130.8±4.3 (std), $T_m$=34.7±2.5 (std), and $\sigma$=29.4±2.1 (std).

Turning to FIG. 3, this figure shows illustrative textures of alginate polymers, including thread-like texture versus more granular texture. For example, the addition of aminoglycoside to sodium alginate and algae extract resulted in more thread-like polymers for neomycin sulfate and kanamycin disulfate, whereas other aminoglycosides showed more granular polymers. In FIG. 3, optical microscopy was used to visualize and quantify polymer texture. To visualize the texture of alginate polymers, reactions on microscopes slides were performed and imaged using an optical microscope at 10× magnification, with the results being shown in FIG. 3.

Because biopolymer texture can affect surface reactions and absorption of ligands, quantitative analysis of polymer may be useful and has been reported for alginate and chitosan films. The polymer texture was quantified using four quantitative parameters (energy, E; contrast, C; homogeneity, H; and entropy, S) of Gray Level Co-Occurrence Matrix (GLCM) algorithm and one quantitative parameter (fractal dimension, F) of Shifting Differential Box Counting (SDBC) algorithm, as described herein. In embodiments, this quantification may advantageously reduce or avoid subjective bias in visual observation. These five parameters were previously used for texture analysis of alginate gel images. The quantitative parameters E, C, H, S, and F were calculated for nine 640 pixel×480 pixel images for each condition. Table 1 shows the quantitative parameters for different aminoglycosides.

Figure 4A:
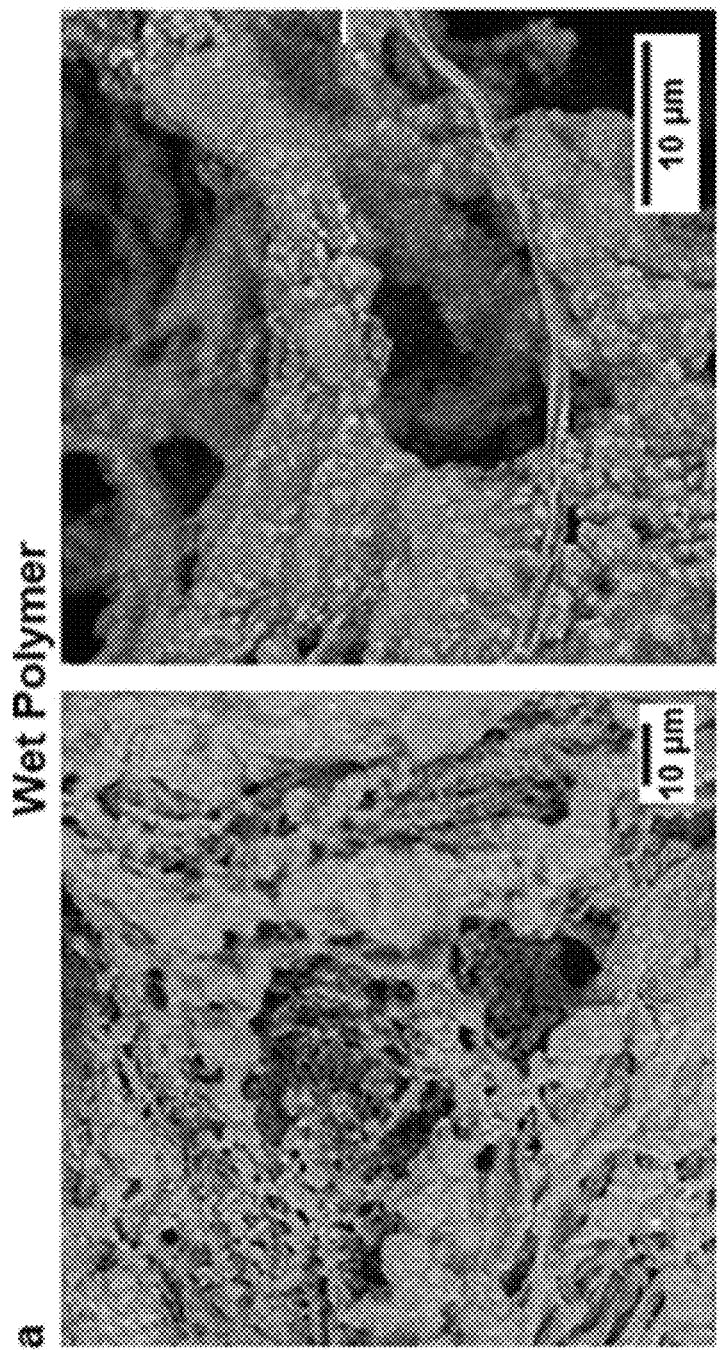
FIG. 4A shows illustrative scanning electron microscope (SEM) images of wet polymer.
Figure 4B:
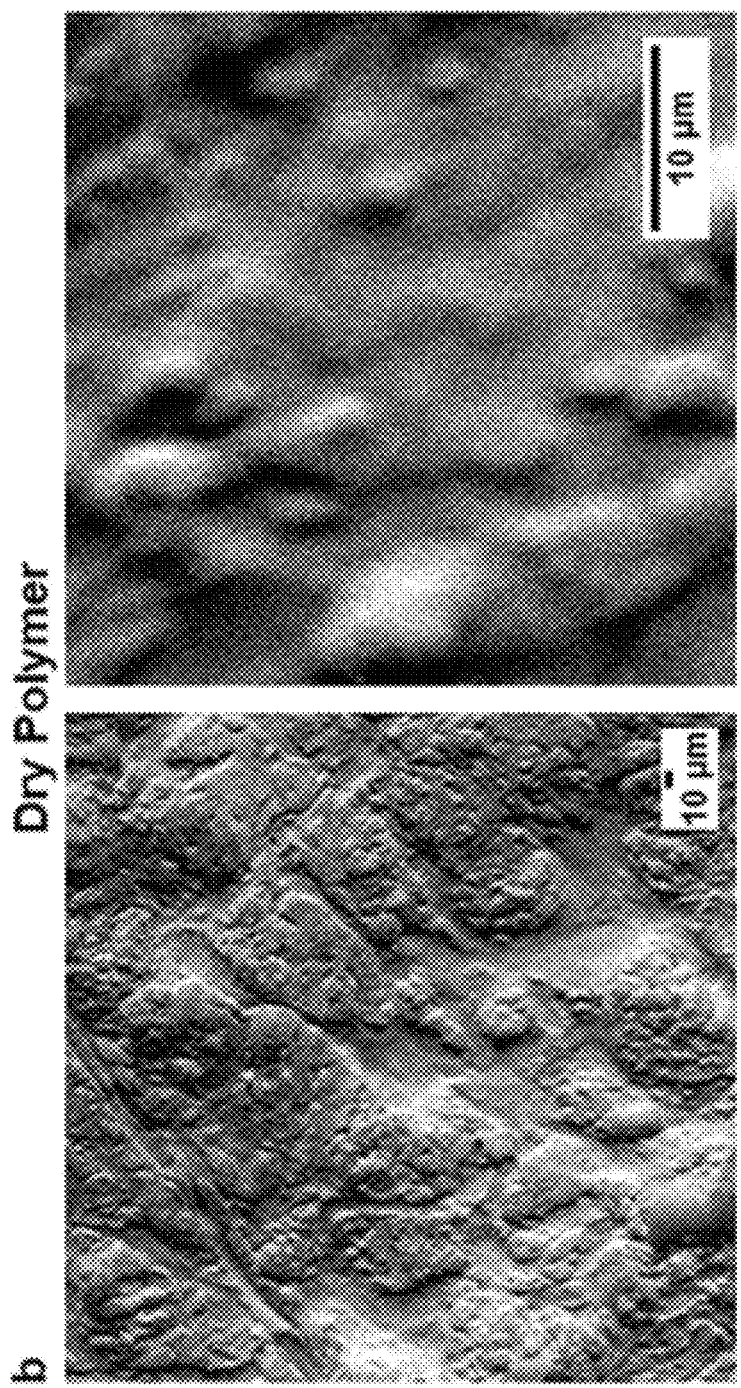
FIG. 4B shows illustrative scanning electron microscope (SEM) images of dry polymer.

As shown in FIGS. 4A and 4B, to determine polymer texture at higher resolutions, KDS-based alginate polymer was imaged using scanning electron microscope (SEM). FIG. 4A shows illustrative SEM images of wet polymer immediately after formation at low resolution (left panel) and high resolution (right panel) and shows threads and porous structures. FIG. 4B shows illustrative SEM images of dry polymer at low resolution (left panel) and high resolution (right panel) and shows a lack of porous structures observed in the wet polymer. Thus, in various embodiments, wet polymer is porous (as shown in FIG. 4A), whereas dry polymer is not porous (as shown in FIG. 4B).

The dry weight of the pellet after centrifugation of polymerization reaction was used to quantify the total amount of polymer. The quantitative weight-based assay approach was used to quantify the optimum amount to antibiotic and sodium alginate for polymer synthesis. Different concentrations were tested with a fixed concentration of sodium alginate and algae extract. To quantify the total amount of alginate polymer created after adding aminoglycosides to alginate solutions, the reactions were centrifuged. Supernatants were decanted and pellets were dried. Dried polymer weights were measured for different concentrations of aminoglycoside and the results are shown in FIGS. 5A and 5B.

Figure 5A:
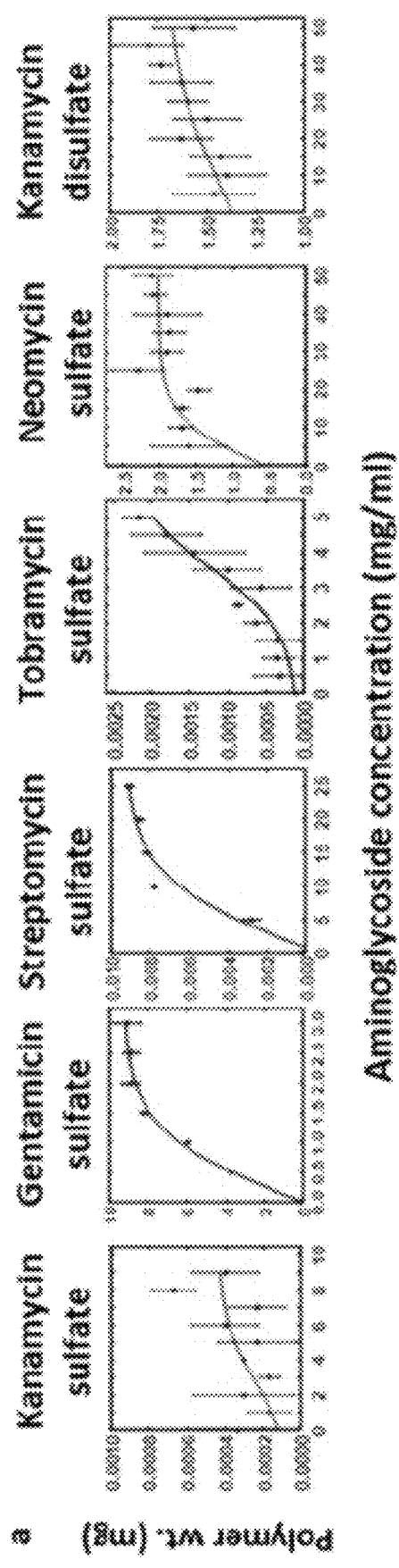
FIG. 5A shows illustrative quantifications of polymer formation for different concentrations of aminoglycosides added to sodium alginate and prion protein-like growth model.
Figure 5B:
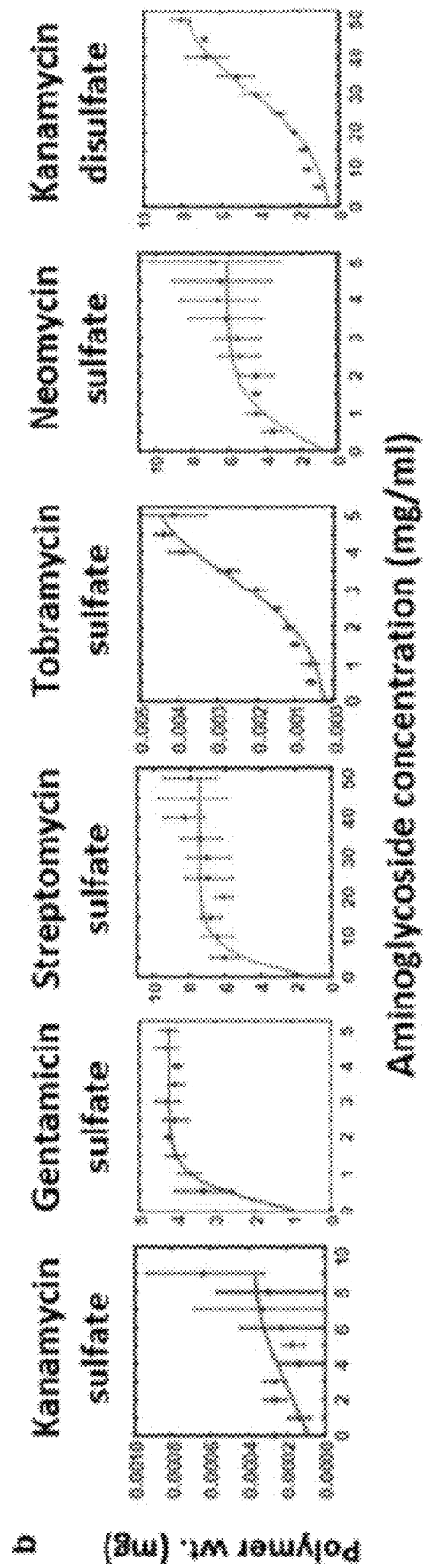
FIG. 5B shows illustrative quantifications of polymer formation for different concentrations of aminoglycosides added to Wakame extract and prion protein-like growth model.

FIGS. 5A and 5B show the quantification of polymer formation for different aminoglycosides and prion protein-like growth model where different concentrations of aminoglycoside were added to sodium alginate (as shown in FIG. 5A) and Wakame extract (as shown in FIG. 5B). The solution was centrifuged and dried to measure the weight of polymer and the experimental polymer weights were fitted against concentrations to a model similar to prion protein growth. Best fit parameters (as shown in Table 2) were used to calculate the dry weight of alginate polymer per mg of antibiotics.

TABLE 1

| Antibiotic | Commercial alginate | | | | |
|---|---|---|---|---|---|
| | E | C | H | S | F |
| GS | 0.0003 ± 0.0002 | 439.1 ± 172.4 | 0.16 ± 0.05 | 9.1 ± 0.2 | 0.23 ± 0.07 |
| KS | 0.0003 ± 0.0001 | 344.4 ± 68.3 | 0.17 ± 0.02 | 8.9 ± 0.2 | 0.27 ± 0.04 |
| NS | 0.0034 ± 0.0048 | 608.8 ± 188.7 | 0.17 ± 0.05 | 9.2 ± 0.5 | 0.20 ± 0.05 |
| SS | 0.0003 ± 0.0001 | 430.6 ± 116.5 | 0.17 ± 0.03 | 9.1 ± 0.3 | 0.21 ± 0.03 |
| TS | 0.0009 ± 0.0001 | 316.1 ± 81.8 | 0.20 ± 0.03 | 9.0 ± 0.3 | 0.28 ± 0.03 |
| KDS | 0.0005 ± 0.0004 | 470.3 ± 13.9 | 0.17 ± 0.03 | 9.2 ± 0.2 | 0.21 ± 0.02 |

| Antibiotic | Algae extract | | | | |
|---|---|---|---|---|---|
| | E | C | H | S | F |
| GS | 0.0003 ± 0.0002 | 282.1 ± 88.4 | 0.17 ± 0.04 | 8.8 ± 0.4 | 0.27 ± 0.06 |
| KS | 0.0007 ± 0.0003 | 253.1 ± 94.5 | 0.23 ± 0.05 | 8.3 ± 0.5 | 0.30 ± 0.05 |
| NS | 0.0005 ± 0.0001 | 114.7 ± 48.0 | 0.25 ± 0.03 | 8.1 ± 0.2 | 0.36 ± 0.04 |
| SS | 0.0004 ± 0.0001 | 384.2 ± 43.18 | 0.18 ± 0.02 | 8.9 ± 0.1 | 0.23 ± 0.03 |
| TS | 0.0003 ± 0.0001 | 201.3 ± 45.2 | 0.18 ± 0.04 | 8.6 ± 0.3 | 0.31 ± 0.04 |
| KDS | 0.0003 ± 0.0001 | 230.3 ± 106.1 | 0.18 ± 0.04 | 8.8 ± 0.3 | 0.29 ± 0.03 |

TABLE 2

| Antibiotic | Commercial alginate | | | | | Algae extract | | | | |
| --- | --- | --- | --- | --- | --- | --- | --- | --- | --- | --- |
| | b | n | r1 | r2 | w | b | n | r1 | r2 | w |
| GS | 0.07 | 1 | 0.59 | −0.62 | 6.3578 | 0.38 | 1 | 0.92 | −1.85 | 3.6457 |
| KS | 1266 | 0.5 | 0.79 | −0.42 | 0.0003 | 878.9 | 0.5 | 0.18 | −0.48 | 0.0003 |
| NS | 0.20 | 1 | 0.20 | −0.36 | 0.6861 | 0.04 | 1 | 0.26 | −0.24 | 4.0841 |
| SS | 50.74 | 0.5 | 0.39 | −0.48 | 0.0002 | 0.05 | 1 | 0.23 | −0.38 | 2.2524 |
| TS | 161.4 | 0.5 | 0.12 | −0.43 | 0.0002 | 61.23 | 0.5 | 0.06 | −0.42 | 0.0005 |
| KDS | 0.28 | 1 | 0.32 | −0.29 | 1.0993 | 0.07 | 3.7 | 0.21 | −0.25 | 0.7823 |

Figure 6:
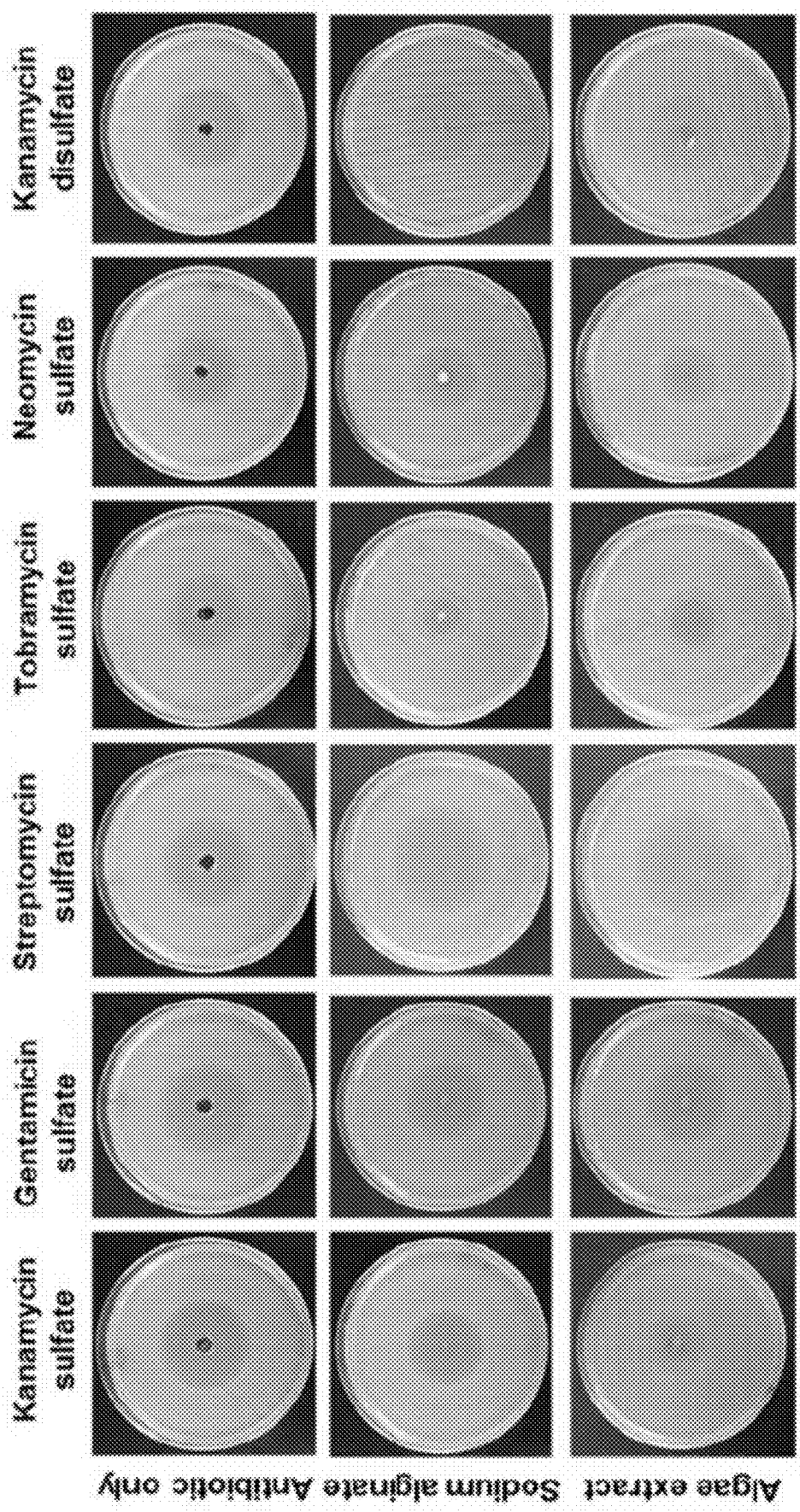
FIG. 6 shows illustrative antimicrobial activity of biopolymers against *E. coli* DH5α.

The antimicrobial property of alginateaminoglycoside polymer against *E. coli* DH5a was quantified by measurement of the zone of bacterial inhibition. In particular, aminoglycoside biopolymers were prepared in microcentrifuge tubes and after centrifugation, pellet was washed three times with sterile deionized water to remove free antibiotic. After washing, the polymer pellet was carefully removed using a spatula and placed at the center of the plate containing *E. coli* DH5αcells and incubated for 18 hr. Circular zones of inhibition were observed against *E. coli* DH5αstrain and are shown in FIG. 6. After incubation for 18 hr, white polymer pellets became transparent to varying degrees.

The antimicrobial activity of biopolymers against *E. coli* DH5α is shown in FIG. 6. In particular, circular zones of growth inhibition are visible after antibiotics and polymers were placed in wells at the centers of LB plates. In FIG. 6, the first row shows results for antibiotics only, the second row shows results for polymer made with sodium alginate, and the third row shows polymer made with algae extract. A higher degree of transparency after incubation generally resulted in large zone of inhibition. While polymers made with KS, GS, and KDS became transparent, polymers made with TS and NS remained white. Alginate polymer made using SS was the most fragile and resulted in the largest zone of inhibition. The diameters of zones of inhibition for different antibiotics against *E. coli* DH5α are given in Table 3.

TABLE 3

| Antibiotics | Commercial alginate | Algae extract | Antibiotic only |
| --- | --- | --- | --- |
| GS | 2.6 ± 1.3 | 2.9 ± 0.1 | 2.9 ± 0.1 |
| KS | 3.7 ± 0.1 | 3.3 ± 0.2 | 3.4 ± 0.1 |
| NS | 2.9 ± 0.1 | 3.0 ± 0.2 | 3.0 ± 0.2 |
| SS | 4.2 ± 0.1 | 3.8 ± 0.1 | 3.5 ± 0.1 |
| TS | 2.6 ± 0.1 | 3.0 ± 0.1 | 3.1 ± 0.1 |
| KDS | 3.0 ± 0.2 | 3.0 ± 0.2 | 3.0 ± 0.1 |

Further, COS-1 cells were grown on alginate polymer. As shown in FIG. 7, COS-1 cells attached, grew, and formed a nest of polymer. The presence of viable cells clearly indicated that aminoglycoside-based alginate polymer is not toxic to COS-1 cells.

Based on the Examples and their results discussed herein, algae extract and commercially available sodium alginate showed similar polymerization behaviors with aminoglycosides. In various embodiments, sodium alginate polymerizes due to acid-base reaction mechanism and a likely mechanism of polymerization is interactions between sodium ions in alginate polymer and sulfate ions in aminoglycoside antibiotics. Thus, after addition of aminoglycoside in sodium alginate, the sulfate ions bind the sodium ions to form sodium sulfate and aminoglycoside binds alginate via amine-carbonyl interactions. Such binding can occur immediately upon the addition of the aminoglycoside in sodium alginate. The addition of polymer in the sodium hydroxide solution reversed the interaction, which was proved by adding sodium hydroxide in polymer pellet followed by heating for 30 min.

The polymerization efficiency can depend on the type of aminoglycoside. Thus, considerations include the cost of aminoglycosides and the amount of alginate polymer produced using 1 mg of aminoglycoside to determine the efficiency of polymerization (which follows the sequence GS>NS>SS>TS>KS>KDS in the decreasing order of efficiency). However, in various embodiments, KDS advantageously results in the most malleable and form fitting polymers. According to the mechanism of polymerization described herein, both the number of amines and sulfate should affect polymerization. While there is a general trend to support the importance of amines and sulfate, the order does not follow exactly, therefore suggesting that there are other factors in polymerization.

The growth of alginate polymer can be similar to a model of prion protein growth where, in general, alginate undergoes complex hierarchical crosslinking and aggregation typical of polysaccharides. For example, alginate polymerization similar to the pathogenic form of prion protein was modeled because both are unbranched linear polymers and form stable aggregates. Experimentally, 30 min were allowed to pass to account for the initial time-dependent polymerization so that the total amount of time-independent alginate polymer can be illustratively described by:

$$y = n - \frac{1}{2} + \frac{r1-r2}{2b} \times \tanh\left[\frac{r1-r2}{2}x + \frac{1}{2}\ln\left(\frac{(r1-r2)+b(1-2n+2y(0))}{(r1-r2)-b(1-2n+2y(0))}\right)\right]$$

where y is the total alginate polymer, y(0) is the initial size of alginate polymers, n represents the minimum size of stable alginate polymers, r1 and r2 are the growth and dissociation rates of alginate polymers, and b is the breakage rate of a alginate polymeric chain. As shown in FIG. 3, this model can fit polymer weights well as a function of concentrations for all the aminoglycosides.

Figure 8:
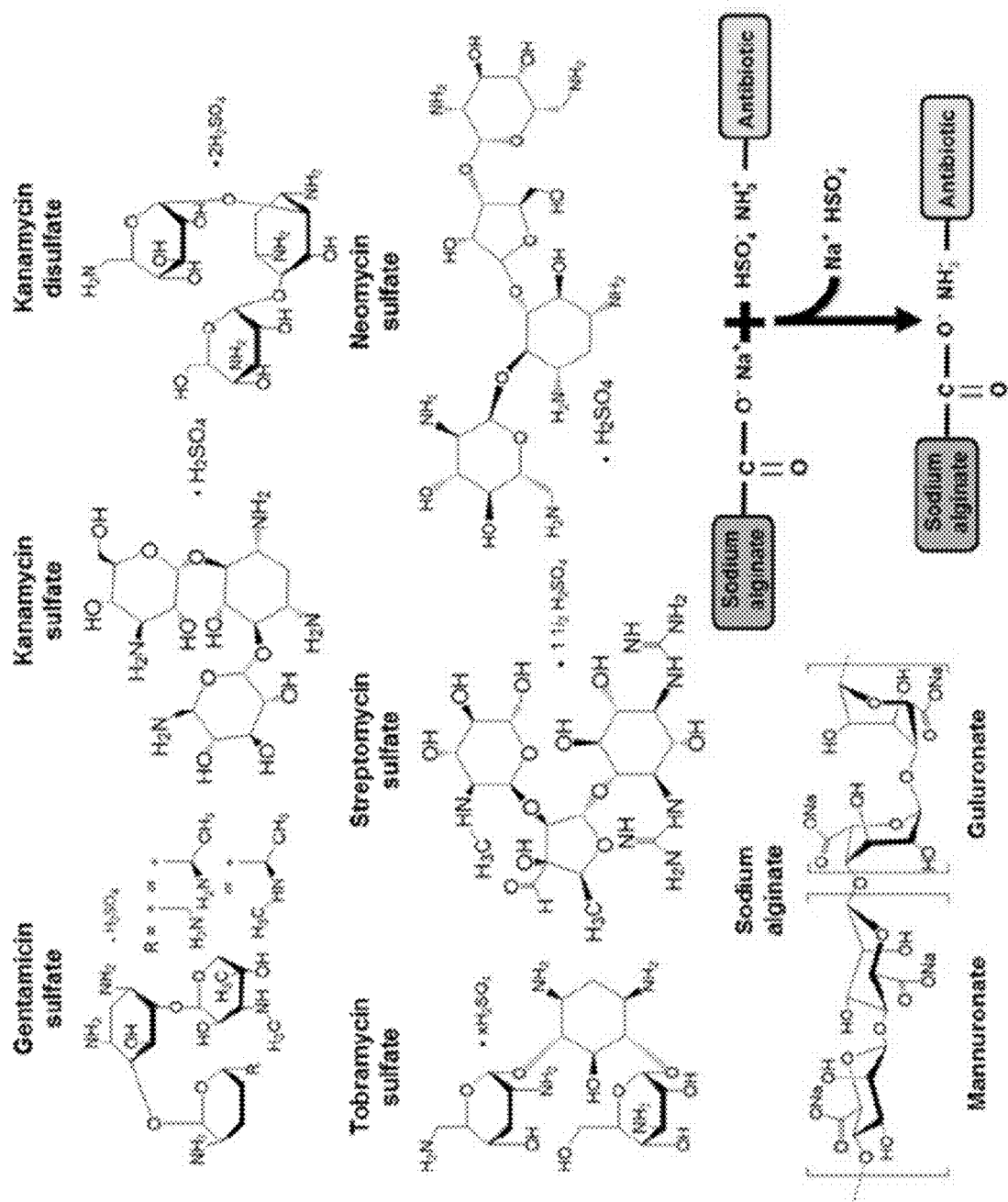
FIG. 8 shows illustrative chemical structures of aminoglycosides and mechanism of aminoglycoside-based alginate polymer.

Further, heat-induced dissociation can result in a slow release of aminoglycoside from alginate biopolymers. For example, FIG. 8 shows chemical structures of aminoglycosides and mechanisms of forming aminoglycoside-based alginate polymer. In particular, since the alginate polymerization occurs due to electrostatic interactions in water (as shown in FIG. 8), the bond strength is similar to hydrogen bonds. As such, thermal breathing of bonds between aminoglycoside and alginate can be possible similar to thermal breathing of hydrogen bonds in deoxyribonucleic acid (DNA), which provides a plausible mechanism of slow release of aminoglycoside from alginate biopolymers. When a piece of aminoglycoside-based alginate polymer is placed at the center, aminoglycosides stochastically detaches from alginate due to thermal breathing and quickly diffuses away driven by the concentration gradient. Since streptomycin sulfate has only two amines, it detaches easily from alginate polymer and leads to highest zone of inhibition (as shown in FIG. 6). In contrast, neomycin sulfate has six amines that leads to a greater chance of attachment after detachment due to thermal breathing. As a result, neomycin sulfate provides more stable alginate polymer and slower release leading to a smaller zone of inhibition (as shown in FIG. 6). Thus, release time can possibly be controlled by the number of sulfate ions in aminoglycosides because it can be theorized that, similar to the number of amines, there can be more reversible detachment with more sulfate ions.

As described herein, embodiments include a one-step method of making antimicrobial alginate polymer using aminoglycosides that is inexpensive and enables slow release of antibiotics, gentamicin sulfate (GS), neomycin sulfate (NS), kanamycin sulfate (KS), kanamycin disulfate (KDS), tobramycin sulfate (TS), and streptomycin sulfate (SS) were screened for polymerization efficiency and antimicrobial activity of the synthesized polymer. Both an aqueous extract of *Undaria Pinnatifida* (Wakame) and aqueous solution of sodium alginate (SA) showed similar polymerization behavior. The growth of the alginate polymer analogous to that of pathogenic prion protein was modeled. Advantageously, slow release of antibiotic, possibly due to thermal breathing, led to clear zones of inhibition against *E. coli* DH5α in agar diffusion assay. This disclosure and results obtained as described herein provide an enabling methodology for further research utilizing alginate/aminoglycoside polymers on antimicrobial wound dressings, artificial skin tissue, artificial antimicrobial blood clot agent, food packaging system, cosmetics, and waste water treatment systems.

Thus, antimicrobial biopolymers provide various advantages, including a biodegradable, sustainable, safe, and cheap approach to drug delivery and wound dressing to control bacterial infection and improve wound healing respectively. Embodiments disclosed herein advantageously provide a one-step method of making antimicrobial alginate polymer from sodium alginate and aqueous extract of Wakame using antibiotic aminoglycosides.

As discussed herein, thin layer chromatography of commercially available sodium alginate and Wakame extract showed similar oligosaccharide profiles. Also, screening of the six aminoglycosides showed that kanamycin disulfate and neomycin sulfate produces the highest amount of biopolymer; however, kanamycin disulfate advantageously produces the most malleable and form fitting biopolymer. Image texture analysis of biopolymers showed similar quantification parameters for all of the six aminoglycosides. Weight of alginate polymer as a function of aminoglycoside concentration follows a growth model of prion protein, consistent with the aggregating nature of both processes. Slow release of antibiotics and the resulting zone of inhibition against *E. coli* DH5α were observed by agar well diffusion assay. Advantageously, as described herein, less expensive methods of production and slow release of antibiotics can enable diverse applications of antimicrobial alginate biopolymer. Also, flexible, porous, and biocompatible aminoglycoside-based alginate polymer as described herein provide an improved (e.g., due to ease of production and/or use) alternative niche for tissue engineering without added chemicals.

Various methods of preparing antimicrobial alginate polymer from aqueous solution of commercial sodium alginate and aqueous extract of Wakame using aminoglycoside antibiotics are described in various embodiments disclosed herein. In embodiments, the underlying acid-base mechanism involves interactions between negatively charged oxygen due to dissociated sodium ions in alginate and protonated amine in aminoglycosides. Polymerization efficiency may loosely correlate with the number of amines and sulfate ions in aminoglycosides. Slow release of aminoglycosides from alginate polymers is evident from the microbial zone of inhibition. Thus, antimicrobial alginate polymers from Wakame, one of the most invasive species in the world that grows in diverse conditions of vast oceans, advantageously provides a sustainable and biodegradable alternative for wound dressing with slow release of antibiotics.

Ranges have been discussed and used within the forgoing description. One skilled in the art would understand that any sub-range within the stated range would be suitable, as would any number within the broad range, without deviating from the invention.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed:

1. A polymer, comprising:
   a sodium alginate; and
   an aminoglycoside, wherein the polymer is used to heal a wound.

2. The polymer of claim 1, wherein the sodium alginate comprises *undaria pinnatifida*.

3. The polymer of claim 1, wherein the aminoglycoside comprises kanamycin disulfate.

4. The polymer of claim 2, wherein the aminoglycoside comprises kanamycin disulfate.

5. The polymer of claim 1, wherein the aminoglycoside comprises neomycin sulfate.

6. The polymer of claim 1, wherein the polymer is applied to a bandage on wound site.

7. The polymer of claim 1, wherein the polymer is applied to a dressing.

8. The polymer of claim 1, wherein the polymer is applied to skin.

9. A composition for treating a bacterial infection, comprising:
   a polymer, comprising:
      a sodium alginate; and
      an aminoglycoside.

10. The composition of claim 9, wherein the sodium alginate comprises *undaria pinnatifida*.

11. The composition of claim 9, wherein the aminoglycoside comprises kanamycin disulfate.

* * * * *